United States Patent [19]

Embil et al.

[11] Patent Number: 5,985,319
[45] Date of Patent: *Nov. 16, 1999

[54] MULTI-PHASE COMPOSITIONS FOR AN INITIAL AND DELAYED RELEASE OF A VAGINAL MEDICAMENT

[75] Inventors: Koral Embil, Istanbul, Turkey; Oswald Morton, London, United Kingdom

[73] Assignee: EDKO Trading and Representation Company Limited, Istanbul, Turkey

[ * ] Notice: This patent issued on a continued prosecution application filed under 37 CFR 1.53(d), and is subject to the twenty year patent term provisions of 35 U.S.C. 154(a)(2).

[21] Appl. No.: 08/605,070

[22] PCT Filed: Sep. 8, 1994

[86] PCT No.: PCT/GB94/01950

§ 371 Date: Jun. 24, 1996

§ 102(e) Date: Jun. 24, 1996

[87] PCT Pub. No.: WO95/07071

PCT Pub. Date: Mar. 16, 1995

[30] Foreign Application Priority Data

Sep. 8, 1993 [GB] United Kingdom .................. 9318641

[51] Int. Cl.⁶ .......................... A61K 9/127; A61K 31/415
[52] U.S. Cl. ........................... 424/450; 514/398; 514/967
[58] Field of Search ..................................... 514/398, 967; 424/450

[56] References Cited

U.S. PATENT DOCUMENTS

| | | | |
|---|---|---|---|
| 4,690,825 | 9/1987 | Won | 424/501 |
| 4,713,247 | 12/1987 | Sakamoto et al. | 424/461 |
| 4,873,091 | 10/1989 | Jankower et al. | 424/489 |
| 5,045,082 | 9/1991 | Ayer et al. | 604/892.1 |

FOREIGN PATENT DOCUMENTS

| | | |
|---|---|---|
| 0 388 718 | 9/1990 | European Pat. Off. . |
| 0 486 117 | 5/1992 | European Pat. Off. . |
| WO-A-90 07325 | 7/1990 | WIPO . |
| WO-A-92 10998 | 7/1992 | WIPO . |

*Primary Examiner*—Minna Moezie
*Attorney, Agent, or Firm*—Bacon & Thomas

[57] ABSTRACT

The present invention relates to multi-phase compositions for treating vaginal infections, for example, infections caused by *Trichomonas vaginitis*. The compositions, which are preferably formulated as a cream or pessary, comprise a continuous phase containing anti-vaginitis medicament for rapid, initial release and porous particles adapted for the delayed release of anti-vaginitis medicaments. Metronidazole is the preferred anti-trichomal medicament.

13 Claims, No Drawings

MULTI-PHASE COMPOSITIONS FOR AN INITIAL AND DELAYED RELEASE OF A VAGINAL MEDICAMENT

This application is a 371 of PCT/GB94/01950 filed Sep. 8, 1994.

This invention concerns novel pharmaceutical compositions for combating vaginal infections.

It is desirable for a pessary to be able to treat all the common forms of vaginitis, which are most often caused by infection with *Candida albicans, Trichomonas vaginalis* or Gardnerella sp, either singly or mixed. Commonly derivatives of imidazole and nitroimidazole are used to treat such conditions, examples of such drugs being miconazole, clotrimazole, ornidazole, tinidazole and metronidazole, but despite the good activity of these compounds none has so far individually achieved the broad spectrum of activity required to combat all the common types of infection. Other types of drugs used in such infections include nitrofurfuryl derivatives and various antibiotics.

While such drugs have been formulated as pessaries and vaginal tablets, it has been found for metronidazole that the relapse rate with trichomonal infections (i.e. the rate of reappearance of infection after cessation of the medicament) is higher when administered in this way than when administration is by the oral route. Consequently the oral route is now the preferred route for administration of metronidazole, and pessaries containing this compound have been virtually discontinued. This results in mixed vaginal infections being treated by both the oral and vaginal routes, with consequent inconvenience to the patient.

However, the half life of most anti-vaginitis medicaments is generally relatively short, for example six hours, and it is difficult to formulate a medicament which can effectively be administered only once a day. On the other hand, when starting administration, it is preferable to provide a relatively large booster dose of the active substance, so that a delayed release formulation is not entirely satisfactory. Similarly, even when using delayed release, levels of the active substance tend to fall towards the end of the period, for example 24 hours, so that a booster dose may be desirable at intervals during medication.

We have found that it is possible to reconcile the above requirements by providing multiphase formulations comprising a continuous phase containing a relatively large amount of one or more anti-vaginitis medicaments for relatively rapid initial release and containing, dispersed therein, microporous particles containing one or more of the anti-vaginitis medicaments and releasing these over a prolonged period, for example 24 hours.

According to the present invention we provide a pharmaceutical composition for the treatment of vaginitis comprising a continuous phase containing one or more anti-vaginitis medicaments for rapid release and porous particles dispersed therein adapted for delayed release of one or more anti-vaginitis medicaments.

In one embodiment of the invention we provide a cream containing the anti-vaginitis medicament(s) together with porous particles containing one or more of anti-vaginitis medicaments.

The phase in which the medicament(s) are contained may be a conventional cream base, e.g. containing oily or waxy materials such as liquid paraffin, white petroleum or cetyl alcohol, water and one or more surfactants to produce a water-in-oil emulsion. A bactericide such as benzalkonium chloride is conveniently present.

According to a further embodiment of the invention, the compositions take the form of pessaries comprising a pessary base containing the anti-vaginitis medicament(s) and porous particles for delayed release of anti-vaginitis medicament(s).

The pessary base may be of any conventional material for vaginal administration such as glycerol/gelatin glycogelatin, macrogols (polyethylene glycols), natural, synthetic or semisynthetic hard fats, and fractionated palm kernel oil. A particularly preferred material is a hard fat such as cocoa butter (theobroma oil), for instance the range of cocoa butter-based products sold under the trade name Witepsol by Dynamit Nobel, Slough, England.

The pessary base may conveniently contain a surfactant to promote dispersal of the active substances. It may also be advantageous to include a surfactant in the porous particles to aid release of the medicament therein and to promote continuous penetration of the active substances into the mucosal folds.

The surfactant may be a cationic, non-ionic, anionic or amphoteric surfactant although non-ionic surfactants are preferred. Anionic surfactants include salts of long chain alkyl sulphonate esters such as sodium lauryl sulphate, sodium cetostearyl sulphate and sodium tetradecyl sulphate; salts of long chain carboxylic acids such as stearates.

Cationic surfactants include quaternary ammonium or pyridinium compounds such as benzalkonium chloride (a mixture of benzyl alkyl dimethyl chlorides, the alkyl chain ranging from $C_8$ to $C_{18}$), tetradecyltrimethyl ammonium bromide and cetylpyridinium chloride.

Amphoteric surfactants include lauryl 1-carboxy glycine and lecithins such as soya lecithin.

Non-ionic surfactants include glycol and glycerol esters such as glyceryl monostearate; macrogol esters and ethers such as cetomacrogol; sorbitan and mannitan esters such as sorbitan tristearate; and polyoxyethylene derivatives of such sorbitan esters, for instance polyoxyethylene (20) sorbitan mono-oleate.

The level of surfactant required in the pessary formulation will be readily determined by those skilled in the art and will depend on the specific surfactant and the nature of the pessary base; conveniently it is in the range 0.1 to 10 percent by weight, preferably 1 to 5 percent.

It is especially preferred to use a cetomacrogol surfactant in conjunction with a cocoa-butter base such as Witepsol. In such a formulation the surfactant is suitably present in the range 1 to 5 percent by weight, for instance about 40 mg in an overall pessary weight of 2540 mg (including active ingredients).

In general, the active substances should include at least one medicament active against *Trichomonas vaginalis*.

Thus one aspect of the invention provides a pessary for human administration comprising an effective amount of one or more drugs active against *Trichomonas vaginalis*, a pessary base and a surfactant.

The preferred antitrichomonal drug is metronidazole.

The use of a surfactant according to the invention allows the active antitrichomonal drug fully to penetrate between the apposed layers of vaginal epithelium which occur in the rugose surface of the vagina so reaching the Trichomonas sp. which otherwise would be protected by such apposition from contact with the active ingredients of conventional pessary formulations. The relapse rate when treatment ceases can therefore be expected to be lower than when metronidazole is administered intravaginally in a conventional pessary formulation.

In order to produce a broad spectrum of activity against vaginal infections, it is desirable to include one or more drugs active against *Candida albicans* and/or Gardnerella sp. This is particularly desirable since administration of metronidazole alone sometimes results in proliferation of infecting fungal pathogens. A fungicidally active derivative of nitroimdazole such as butoconazole or, more preferably, miconazole, is advantageously used as the drug active against *Candida albicans*. Ornidazole, Ketoconazole, Tioconazole and Tinidazole are also suitable fungicidally active agents. Where metronidazole is used as the antitrichomonal drug, it will also be effective against Gardnerella sp. However, a broad spectrum antibiotic such as pivampicillin or Clindamycin may advantageously also be included. In order to counter the inflammation and itching associated with vaginitis, it may be beneficial to include a steroidal or non-steroidal antiinflammatory drug such as hydrocortisone or ibuprofen. Lactic acid may also advantageously be included as a further active ingredient.

The pessaries of the present invention may also advantageously include chlorophyll as a deodorant. We have found that although some staining of clothes by the green coloration of the chlorophyll may take place, the surfactant in the composition ensures that such stains are readily removed.

The quantity of metronidazole is conveniently from 500 to 1500 mg per pessary, more preferably from 800 to 1200 mg and suitably about 1000 mg.

The pessary may conveniently contain from 200 to 600 mg of miconazole, more preferably from 240 to 480 mg. The miconazole may be in the form of the free base, especially in the porous particles, or as a salt, for instance the nitrate, especially in the pessary base—a suitable quantity of miconazole per pessary is then about 400 mg.

The porous particles containing anti-vaginitis medicaments may contain two or more such medicaments and/or the composition may contain mixtures of porous particles each containing a different medicament or mixtures of medicaments.

A wide range of porous particles are available, as described in International Patent Applications WO88/01164 and WO89/10132, U.S. Pat. Nos. 4,873,091 and 4,690,825 and EP-A-306236, the contents of which are incorporated herein by reference.

In such porous particles, the total pore volume is preferably in the range 0.1 to 2.0 ml/g, more preferably 0.3 to 1.0 ml/g. The diameters of the particles will generally be in the range 1 to 1000 microns, preferably 5 to 100 microns, more preferably 10 to 50 microns: the surface area of the particles will generally range from about 1 to 500 $m^2/g$, preferably 20 to 200 $m^2/g$.

The porous particles may be composed of a wide range of materials. Many organic, synthetic polymers are suitable, as well as natural substances such as cellulose or gelatin. The choice of material will depend in part on the intended means of delayed release of the active medicament, i.e. diffusion, compression, dissolving or melting.

Where diffusion of the active medicament is intended, the porous particles may be relatively rigid. This has the advantage that the outermost pores do not collapse when the medicament diffuses out and thus do not block the diffusion of the medicament from the inner pores. Such rigidity can be controlled by the degree of cross-linking of polymeric materials of which the particles are composed. The degree of cross-linking will generally be at least 10%, more usually in the range 20 to 80%, for example 25 to 60%.

Polymers of which the particles may be formed include polyolefins, including polyethylene, polystyrene, polydicyclopentadiene etc.; polyacrylate esters, e.g. optionally alkoxylated $C_{1-10}$ alkyl, cycloalkyl, aryl or aralkyl esters of polyacrylic or polymethacrylic acids; polyvinyl esters e.g. polyvinyl acetate or polyvinyl laurate; polyvinyl ketones, e.g. polyvinylmethyl ketone; and polyvinyl ethers, e.g. polyvinylpropyl ether.

As indicated above, the porous particles in such a cream may liberate the active medicament by diffusion, pressure, dissolving or melting. It is preferred that the particles are elastically compressable so that after first application of the cream whereby the medicament contacts the infected area, application of gentle pressure, for example by rubbing, causes rapid release of the active medicament to provide a coating of medicament over the layer of cream.

Elastically compressable particles may be composed of elastomers, such as those described in U.S. Pat. No. 4,873,091, including for example, isoprene rubbers, butadiene rubbers, chloroprene rubbers, styrene butadiene. Particularly useful are ethylene-propylene-diene terpolymers, wherein the diene components may be straight chain diolefins, cyclic dienes and bicyclic dienes. Examples of such dienes include 1,4-hexadiene, dicyclopentadiene and ethylidene norbornene. Silicone rubbers may also be used.

Porous particles which dissolve, primarily in aqueous body fluids, may be composed of water-soluble gels including gelatin, agarose etc and certain polymethyl methacrylates such as Eudragit (Röhm, Darmstadt) which dissolve at the pH of the vagina.

Porous particles which melt may be composed of fats and waxes of the type used in suppositories which melt at body temperatures but which are solid at room temperature as well as gelatin.

Porous materials for use in compositions of the invention may be made in any convenient way. Thus, it is possible to polymerise one or more suitable monomers in the presence of a dispersed porogen: after polymerisation, the porogen may be removed, e.g. by evaporation or solvent extraction, to provide a network of interconnected pores. The active medicament can then be absorbed into the porous material, if desired by first evacuating air from the pores. The active medicament can, however, itself be used as the porogen: the medicament may be dispersed in droplets through a monomer with which it is immiscible so that after polymerisation the active medicament effectively fills pores within the polymeric material. In general, however, it is preferred to prepare the porous material first in order to remove rigorously all traces of monomer, catalysts and cross-linking agents, before introduction of active medicament.

A number of possible methods of manufacture of porous material, in particular porous particles, are described in the prior patents listed above.

In general, porous particles may conveniently be produced by emulsion or suspension polymerisation in a liquid—liquid system. Thus, for example, a solution comprising the chosen water-immiscible monomer, any cross-linking agent required, a catalyst, if needed, and a porogen which is miscible with the solution but immiscible with water. The solution is then suspended in an aqueous solution, which may contain one or more suspending agents or surfactants and polymerisation is initiated e.g. by raising the temperature or by irradiation. The porogen is then removed from the solidified particles, e.g. by evaporation or extraction into a solvent which is substantially inert to the polymer.

Examples of such porogens include $C_{5-12}$ alkanes, $C_{5-8}$ cycloalkanes and aromatic solvents such as benzene toluene etc. The particles will normally be washed thoroughly to remove contaminants, using solvents such that the final solvent can be removed by evaporation.

In general, particle diameter may be controlled by the degree of agitation to prepare the initial emulsion. The pore diameter and pore volume are controlled by the amount of porogen used and the degree of cross-linking.

The monomers used to prepare the particles may be any of those appropriate to make the polymers set out above. Suitable cross-linking agents for mono-olefins include polyethylenically unsaturated monomers.

The dosage of active medicament(s) contained in the porous particles will vary with the individual medicaments and their half-lives. In general, the ratio of delayed release medicament to rapid release medicament is preferably in the range 1:1 to 5:1, for example 2:1 to 4:1.

The porous particles may be evenly distributed throughout the composition or, in the case of pessaries, may be concentrated in one or more zones, for example in a core.

In general, the size of the porous particles is preferably such that they cannot be taken up into the lymph ducts. On the other hand, large particles give a gritty effect which may produce discomfort. In general, the preferred size range for the porous particles is 10–100 microns.

The following Examples are given by way of illustration only:

EXAMPLE 1

Pessary

Composition of Pessary base

| | |
|---|---|
| Metronidazole | 250.0 mg |
| Miconazole nitrate | 50.0 mg |
| Witepsol w35 | 1745.4 mg |
| Cetomacrogol | 34.6 mg |
| | 2080.0 mg per pessary |

Composition of Microsponges

| | |
|---|---|
| Metronidazole | 500.0 mg |
| Miconazole | 100.0 mg |
| both held within polystyrene-divinylbenzene porous beads, pore volume 0.5 ml/g | |

Method of Manufacture

The two active ingredients and the surfactant of the base are mixed into the molten Witepsol w35 and the resulting mixture is blended with the pre-prepared porous beads before being poured into pre-cooled moulds. The moulds are passed through a cooling tunnel at −10° C., the pessaries are removed from the moulds and packaged. 0.1% by weight of chlorophyl may be added to both base and microsponge phases.

EXAMPLE 2

Pessary

Composition of Pessary Base

| | |
|---|---|
| Polyethylene glycol 4000 | 900.0 mg |
| Polyethylene glycol 1000 | 450.0 mg |
| Polyethylene glycol 400 | 118.5 mg |
| MONATERIC 951A | 42.0 mg |
| metronidazole | 250.0 mg |
| Tioconazole hydrochloride | 100.0 mg |
| pivanpicillin | 100.0 mg |
| | 1960.5 mg per pessary |

MONATERIC is a surfactant available from Mono Industries Ltd., Paterson, N.J., U.S.A.

Composition of Porous Beads

| | |
|---|---|
| Metronidazole | 500.0 mg |
| Tioconazole | 200.0 mg |
| Hydrocortisone | 50.0 mg |
| Pivampicillin | 50.0 mg |
| blended together and held within a polystyrenedivinylbenzene porous beads, pore volume 0.5 ml/g | |

The pessary is prepared according to the method of Example 1. The MONATERIC 951A may be replaced by MONAQUAT PT-C, PT-L, PT-S or Phospholipid EFA.

EXAMPLE 3

Pessary

| | |
|---|---|
| Polystyrene-divinylbenzene porous beads (mean particle diameter 30 microns, pore volume 0.5 ml/g) containing 2 g miconazole and 10 g metronidazole | 25 g |
| 50% Benzalkonium chloride | 0.2 g |
| Hydrocortisone acetate | 0.5 g |
| Metronidazole | 12.5 g |
| Miconazole | 2.5 g |
| Witepsol S55 suppository base | 63.65 g |
| Witepsol E85 suppository base | 10.65 g |

The above components apart from the porous particles containing their active ingredients are blended at 55° C., cooled to 40° C. and poured into 50 moulds with central pins to make the pessaries formed hollow. After cooling, the pins are withdrawn, the moulds are inverted and porous particles introduced into the cavity left by each pin. The remainder of the cavity is filled with a blend of the two Witepsol bases at 40° C. After chilling, the pessaries are removed from the moulds and packaged.

EXAMPLE 4

Cream

| | % |
|---|---|
| Polystyrene-divinylbenzene porous beads (mean particle diameter 30 microns, pore volume 0.5 ml/g) containing 2 g miconazole and 10 g metronidazole | 25.0 |
| Liquid paraffin | 17.75 |
| White petrolatum | 8.0 |
| Cetyl alcohol | 7.0 |
| Span 60 | 3.0 |
| Miconazole | 0.5 |
| Metronidazole | 2.0 |
| Potassium dihydrogen phosphate | 0.5 |
| 1% Aqueous Benzalkonium chloride | 10.0 |
| Tween 60 | 5.0 |
| 70% Aqueous sorbitol | 5.0 |
| Hydrocortisone acetate | 0.5 |
| Water | 15.75 |

The oily phase comprising the liquid paraffin, white petrolatum, cetyl alcohol and Span 60 are mixed at 60° C. The aqueous phase comprising the remaining components except the porous beads is also blended at 60° C. and the two phases combined and homogeneously blended. The porous beads are added subsequently and dispersed throughout the cream.

EXAMPLE 5

Pessary

Composition of Pessary Base

| | |
|---|---|
| Metronidazole | 250.0 mg |
| Miconazole nitrate | 50.0 mg |
| Witepsol w35 | 1745.4 mg |
| Cetomacrogol | 34.6 mg |
| | 2080.0 mg per pessary |

Composition of Microsponges

| | |
|---|---|
| Metronidazole | 500.0 mg |
| Miconazole | 100.0 mg |
| Sorbitan mono-oleate | 190.0 mg |
| each held within polystyrene-divinylbenzene porous beads, pore volume 0.5 ml/g | |

The pessary is prepared according to the method of Example 1.

We claim:

1. A multi-phase pharmaceutical composition for topical administration in the form of a cream or pessary for the treatment of vaginitis comprising a continuous phase containing two or more anti-vaginitis medicaments for rapid initial release and dispersed therein porous particles adapted for the delayed release of two or more anti-vaginitis medicaments, and wherein the medicaments for both rapid and delayed release are metronidazole together with one or more drugs active against *Candida albicans* and /or Gardneralla sp.

2. A composition as claimed in claim 1 further comprising a surfactant.

3. A composition as claimed claim 1 in the form of a cream.

4. A composition as claimed claim 1 in the form of a pessary.

5. A pharmaceutical composition as claimed in claim 1 wherein the ratio of delayed release medicament to rapid initial release medicament is in the range 1:1 to 5:1.

6. A composition as claimed in claim 5 wherein the ratio is in the range 2:1 to 4:1.

7. A pharmaceutical composition as claimed in claim 4 wherein the pessary comprises a core in which the porous particles are concentrated.

8. A composition as claimed in claim 4 wherein the continuous phase comprises about 250 mg of metronidazole and about 50 mg of miconazole nitrate as active ingredients, and wherein the porous particles comprise about 500 mg of metronidazole and about 100 mg of miconazole nitrate as active ingredients.

9. A composition as claimed in claim 4 wherein the continuous phase comprises about 250 mg of metronidazole, about 100 mg of tioconazole hydrochloride, and about 100 mg of pivampicillin as active ingredients, and wherein the porous particles comprise about 500 mg of metronidazole, about 200 mg of tioconazole hydrochloride, about 50 mg of hydrocortisone, and about 50 mg of pivampicillin as active ingredients.

10. A composition as claimed in claim 2, wherein the surfactant is a cetomacrogol surfactant and the composition contains a pessary base which is a hard fat cocoa-butter.

11. A composition as claimed in claim 1 wherein said medicaments are metronidazole and miconazole.

12. A composition as claimed in claim 1 which additionally includes one or more medicaments selected from a broad spectrum antibiotic, an anti-inflammatory drug and a bactericide.

13. A method of treatment of vaginitis, said method comprising administering intravaginally a composition as claimed in claim 1.

* * * * *